(12) United States Patent
Mathew et al.

(10) Patent No.: US 7,361,772 B2
(45) Date of Patent: Apr. 22, 2008

(54) PROCESS FOR THE PRODUCTION OF ATORVASTATIN CALCIUM

(75) Inventors: Joy Mathew, Karnataka (IN); Madhavan Sridharan, Karnataka (IN); Sambasivam Ganesh, Karnataka (IN); Tom Thomas Puthiaparampil, Karnataka (IN)

(73) Assignee: Biocon Limited, Bangalore (IN)

( * ) Notice: Subject to any disclaimer, the term of this patent is extended or adjusted under 35 U.S.C. 154(b) by 74 days.

(21) Appl. No.: 10/483,484

(22) PCT Filed: Oct. 7, 2003

(86) PCT No.: PCT/IN03/00328

§ 371 (c)(1),
(2), (4) Date: Oct. 26, 2005

(87) PCT Pub. No.: WO2005/033078

PCT Pub. Date: Apr. 14, 2005

(65) Prior Publication Data

US 2006/0084816 A1 Apr. 20, 2006

(51) Int. Cl.
*C07D 207/333* (2006.01)
(52) U.S. Cl. .................................................. 548/537
(58) Field of Classification Search ................ 548/537
See application file for complete search history.

(56) References Cited

U.S. PATENT DOCUMENTS

| 6,274,740 B1 | 8/2001 | Lin et al. |
| 6,528,661 B2 | 3/2003 | Niddam et al. |
| 2002/0099224 A1 | 7/2002 | Niddam et al. |
| 2003/0114685 A1 | 6/2003 | Niddam-Hildesheim et al. |
| 2003/0175338 A1 | 9/2003 | Singh et al. |
| 2005/0119493 A1* | 6/2005 | Suri et al. ................... 548/537 |

FOREIGN PATENT DOCUMENTS

| WO | WO 97/03960 | 2/1997 |
| WO | WO 02/43667 A2 | 6/2002 |
| WO | WO 03/004450 A1 | 1/2003 |
| WO | WO 03/004455 A2 | 1/2003 |
| WO | WO03/004456 | 1/2003 |
| WO | WO 03/016317 A1 | 2/2003 |

OTHER PUBLICATIONS

Hao Fang, Gurpreet Kaur, and Binghe Wang Progress in Boronic Acid-Based Fluorescent Glucose Sensors Journal of Fluorescence; vol. 14, No. 5 / Sep. 2004 Springer Netherlands.*
Bradley D. Smith, Stephen J. Gardiner, Tracey A. Munro, Marie-France Paugman and Jennifer A. Riggs Facilitated Transport of Carbohydrates, Catecholamines, and Amino Acids Through Liquid and Plasticized Organic Membranes Journal of Inclusion Phenomena and Molecular Recognition in Chemistry 32: 121-131, 1998. Kluwer Academic Publishers.*
Yasumasa Kanekiyo and Hiroaki Tao Glucose-specific Sensing with Boronic Acid Utilizing Enzymatic Oxidation Chemistry Letters vol. 35, No. 8 (2006).*
Chawla et. al.; CRIPS vol. 5, No. 1, p. 9-12.*
Newman et. al.; DDT vol. 8, No. 19, p. 898-905.*
Oehrlein R et al., "Chemoenzymatic approach to statin side-chain building blocks" Advanced Synthesis Catalysis (2003), 345 (6+7), 713-715.
Woo et al., "Atorvastatin, an HMG-CoA reductase inhibitor and effective lipid-regulating agent. Part III. Syntheses of [2H5]-, [13C8], and [13C7, 15N] atorvastatin and their application in metabolic and pharmacokinetic studies", Journal of Labeled Compounds Radiopharmaceuticals (1999), 42(2), 135-145.
Lee et al., "Atorvastatin, an HMG-CoA reductase inhibitor and effective lipid-regulating agent. Part II. Synthesis of side chain-labeled [14C] atorvastatin", Journal of Labeled Compounds Radiopharmaceuticals (1999), 42(2), 129-133.
Woo et al., "Atorvastatin, an HMG-CoA reductase inhibitor and effective lipid-regulating agent. Part I. Synthesis of ring-labeled [14C] atorvastatin", Journal of Labeled Compounds Radiopharmaceuticals (1999), 42(2), 121-127.
Radl et al., "An improved synthesis of 1,1-dimethylethyl-6-cyanomethyl-2,2-dimethyl-1,3-dioxane-4-acetate, a key intermediate for atorvastatin synthesis", Tetrahedron Letters (2002), 43(11), 2087-2090.
Manzoni et al., "Biosynthesis and biotechnological production of statins by filamentous fungi and application of these cholesterol-lowering drugs", Applied Microbiology and Biotechnology (2002), 58(5), 555-564.
Roth, Bruce D., "The discovery and development of atorvastatin, a potent novel hypolipidemic agent", Progess in Medicinal Chemistry (2002), 40, 1-22.
Wierzbicki, Anthony S., "Atorvastatin", Expert Opinion on Pharmacotherapy (2001), 2(5), 819-830.
Graul et al., "Atorvastatin calcium", Drugs of the future (1997), 22(9), 956-968.
Baumann et al., "The convergent synthesis of CI-981, an optically active, highly potent, tissue-selective inhibitor of HMG-CoA reductase", Tetrahedron Letters (1992), 33(17), 2283-2284.

* cited by examiner

Primary Examiner—James O. Wilson
Assistant Examiner—Jeffrey H Murray
(74) Attorney, Agent, or Firm—Robin A. Weatherhead; Choate Hall & Stewart, LLP

(57) ABSTRACT

In one aspect, the invention provides a process for the production of 5-(4-Fluoro-phenyl)-2-isopropyl-4-phenyl-1-(3,5,7-trihydroxy-heptyl)-1H-pyrrole-3-carboxylic acid phenylamide hemicalcium salt, stereoisomers thereof or polymorphs thereof from a (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester.

11 Claims, No Drawings

PROCESS FOR THE PRODUCTION OF ATORVASTATIN CALCIUM

PRIORITY CLAIM

The present application claims the benefit under 35 U.S.C. § 371 of International Application No.: PCT/IN03/00328, filed Oct. 7, 2003, the entire contents of this application are hereby incorporated by reference.

FIELD OF THE INVENTION

The present invention relates to a novel process for the production of atorvastatin calcium. Particularly, the present invention relates to a novel process for the production of amorphous atorvastatin calcium from (6-{2-[2-(4-Fluorophenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester.

BACKGROUND OF THE INVENTION

Atorvastatin calcium is known by synonyms like [R-(R*,R*)]-2-(4-fluorophenyl)-σσ, 6-dihydroxy-5-(1-methylethyl)-3-phenyl-4-[(phenylamino) carbonyl-1H-pyrrole-1-heptanoic acid hemicalcium salt; (βR,δR)-2-(4-fluorophenyl)-β,δ-dihydroxy-5-(1-methylethyl)-3-phenyl-4-[(phenylamino)carbonyl]-, 1H-Pyrrole-1-heptanoic acid hemicalcium salt; [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid hemicalcium salt or (βR,δR)-2-(p-Fluorophenyl)-β,δ-dihydroxy-5-isopropyl-3-phenyl-4-(phenylcarbamoyl)pyrrole-1-heptanoic acid hemicalcium salt.

The hemicalcium salt of [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid, a synthetic HMG-CoA reductase inhibitor, is used for the treatment of hyperlipidemia and hypercholesterolemia, both of which are risk factors for arteriosclerosis and coronary heart disease. Open dihydroxy carboxylic acid, lactone and various salt forms of [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid have been synthesized.

U.S. Pat. No. 5,273,995, teaches that [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid has surprising inhibition of the biosynthesis of cholesterol. The calcium salt of [R-(R*,R*)]-2-(4-fluorophenyl)-β,δ-dihydroxy-5-(1-methylethyl)-3-phenyl-4-[(phenylamino) carbonyl]-, 1H-Pyrrole-1-heptanoic acid (2:1) (Formula I)

FORMULA I

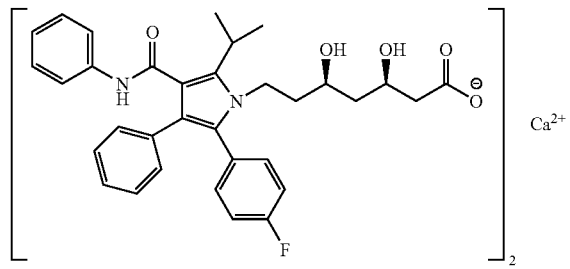

is more suited to formulations and has been recommended as a drug.

U.S. Pat. Nos. 5,003,080; 5,097,045; 5,103,024; 5,124,482; 5,149,837; 5,155,251; 5,216,174; 5,245,047; 5,248,793; 5,273,995; 5,280,126; 5,298,627; 5,342,952; 5,385,929; 5,397,792; European Patent 409,281; and WO 89/07598 describe various processes and key intermediates for preparing atorvastatin.

WO 97/03958 and WO 97/03959 disclose novel crystalline forms of atorvastatin calcium designated as Form I, Form II, Form III and Form IV and methods for their preparation, providing more favorable filtration and drying characteristics.

WO 97/03960 and U.S. Pat. No. 6,087,511 describe procedures for converting the crystalline form of atorvastatin calcium to an amorphous form. The processes disclosed therein involve dissolving Form I atorvastatin calcium in a non-hydroxylic solvent like tetrahydrofuran or a mixture of tetrahydrofuran and toluene.

WO 00/71116 describes a procedure for converting the crystalline Form-I by dissolving it in a non-hydroxylic solvent like tetrahydrofuran and precipitating amorphous atorvastatin calcium by the addition of nonpolar hydrocarbon solvents like, n-hexane, cyclohexane or n-heptane, for example.

It is therefore one object of the present invention to provide a novel process for the preparation of atorvastatin calcium, unique with respect to its simplicity, cost effectiveness and scalability.

SUMMARY OF THE INVENTION

The present invention relates to a novel process for the preparation of atorvastatin calcium.

In one aspect, the process of the present invention comprises converting a compound of Formula II to atorvastatin calcium (Formula I).

FORMULA II

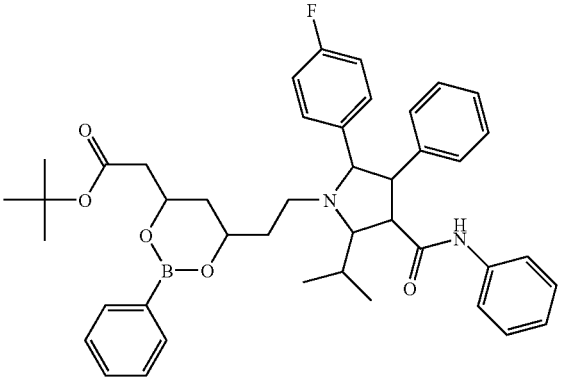

In certain exemplary embodiments, the process comprises treating a compound of Formula II with calcium oxide.

The process of the present invention is novel, simple, inexpensive and industrially scalable.

Advantages of the present invention include: de-protection of a boronate ester, cleavage of a tert-butyl ester and formation of a calcium salt are achieved in one step, employing a single reagent; a simple procedure involving inexpensive CaO is used; and the calcium salt is obtained directly without the need for making sodium salt or any other intermediates, thereby reducing the necessary number of steps.

DETAILED DESCRIPTION OF CERTAIN PREFERRED EMBODIMENTS OF THE INVENTION

In certain embodiments, the novel process of the present invention relates to the preparation of [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid hemicalcium salt.

In one aspect, the process is a simple, one-step, economic and industrially scalable process comprising converting (6-{2-[2-(4-Fluoro-phenyl)-5-isopropyl-3-phenyl-4-phenyl-carbamoyl-pyrrolidin-1-yl]-ethyl}-2-phenyl-[1,3,2]dioxaborinan-4-yl)-acetic acid tert-butyl ester to [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid hemicalcium, its stereoisomers or polymorphic forms.

In one embodiment, the process comprises treating (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester with calcium oxide in a suitable solvent.

In another embodiment, a suitable solvent is selected from water, a water miscible or a water immiscible solvent.

In certain embodiments, the solvent system used may be a single solvent or a mixture of two or more solvents.

In certain other embodiments, the water miscible solvent may be selected from one or more among methanol, ethanol, isopropanol, acetone, THF or acetonitrile, or a combination thereof.

In another aspect, the reaction of the present invention is carried out at suitable reaction conditions required for satisfactory conversion of the starting material to atorvastatin calcium. In one embodiment, the starting material is Formula II.

In yet another aspect, the reaction may be carried out at a temperature between about 25 to 100° C. In one embodiment of this aspect, the reaction is carried out at a temperature between about 40 to 70° C.

The reaction may be carried out for a time period between about 1 to 24 hours. In one embodiment, the reaction is carried out for a time period between about 5 to 15 hours.

After satisfactory conversion, the product may be isolated with or without further purification.

The present invention will now be illustrated by the following examples, which are not intended to limit the effective scope of the claims. Consequently, any variations of the invention described above are not to be regarded as departure from the spirit and scope of the invention as claimed. The present invention has been described in terms of its specific embodiments and various modifications and equivalents will be apparent to those skilled in the art and are intended to be included within the scope of present invention.

EXAMPLE 1

A mixture of (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester (5 g, 0.007 mol), water (200 ml), methanol (200 ml) and calcium oxide (5.0 g, 0.09 mol) was stirred at 50-60° C. for 10 hours. After filtering the reaction mixture, the resulting clear filtrate was concentrated to about 150 ml and washed with methyl tert-butyl ether (50 ml). The aqueous layer was evaporated and the solid obtained was dissolved in THF (50 ml). The solution was filtered and concentrated to yield [R-(R*,R*)]-2-(4-fluorophenyl)-β,δ-dihydroxy-5-(1-methylethyl)-3-phenyl-4-[(phenylamino)carbonyl]-, 1H-Pyrrole-1-heptanoic acid hemicalcium salt.

EXAMPLE 2

A mixture of (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester (50 g, 0.07 mol), water (2 L), THF (2 L) and calcium oxide (50 g, 0.9 mol) was stirred at 50-60° C. for 8 hours. After filtering the reaction mixture, the resulting clear filtrate was concentrated to about 1.5 L and washed with methyl tert-butyl ether (500 ml). The aqueous layer was evaporated and solid obtained was dissolved in THF (500 ml). The solution was filtered and concentrated to yield atorvastatin calcium.

EXAMPLE 3

A mixture of (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester (100 g, 0.14 mol), water (3.0 L), acetonitrile (3.0 L) and calcium oxide (75 g, 1.35 mol) was stirred at 50-60° C. for 12 hours. After filtering the reaction mixture, the resulting clear filtrate was concentrated to about 3.0 L and washed with methyl tert-butyl ether (1.0 L). The aqueous layer was evaporated and the solid obtained was dissolved in acetonitrile (1.0 L). The solution was filtered and concentrated to yield [R-(R*R*)]-2-(4-fluorophenyl)-β,δ-dihydroxy-5-(1-methylethyl)-3-phenyl-4-[(phenylamino)carbonyl]-, 1H-Pyrrole-1-heptanoic acid hemicalcium salt.

We claim:

1. A process for the preparation of a compound of Formula I:

FORMULA I

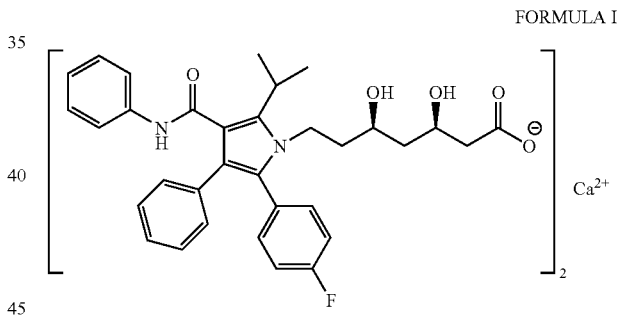

the process comprising the step of:
treating a compound of Formula II

FORMULA II

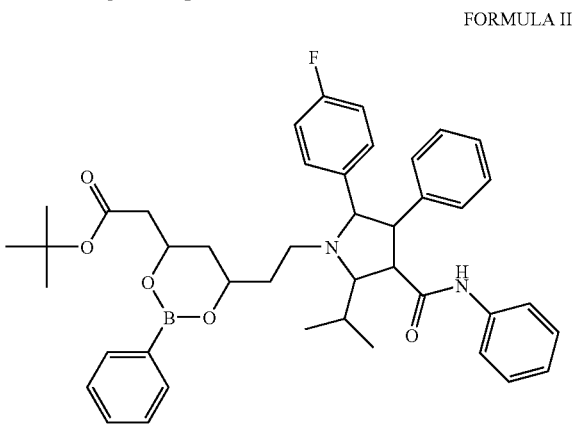

with a source of calcium ion.

2. The process of claim 1, wherein the source of calcium ion is CaO or Ca(OH)$_2$.

3. The process of claim 1, wherein the treating step is carried out in a solvent.

4. The process of claim 3, wherein the solvent is water, a water miscible solvent or a water immiscible solvent.

5. The process of claim 3, wherein the solvent is water or a water miscible solvent.

6. The process of claim 4, wherein the solvent is a single solvent or a mixture of two or more solvents.

7. The process of claim 6, wherein the solvent is selected from at least one of methanol, ethanol, isopropanol, acetone, acetonitrile or THF.

8. The process of claim 1, wherein the treating step is carried out at a temperature between about 25 to 100° C.

9. The process of claim 8, wherein the treating step is carried out at a temperature between about 40 to 70° C.

10. The process of claim 1, wherein the treating step is carried out for a time period between about 1 to 24 hours.

11. The process of claim 1, wherein the treating step is carried out for a time period between about 1 to 10 hours.

* * * * *